United States Patent [19]

Martindale

[11] Patent Number: 4,806,700
[45] Date of Patent: Feb. 21, 1989

[54] PRODUCTION OF BENZENE FROM LIGHT HYDROCARBONS

[75] Inventor: David C. Martindale, Roselle, Ill.
[73] Assignee: UOP Inc., Des Plaines, Ill.
[21] Appl. No.: 921,307
[22] Filed: Oct. 22, 1986
[51] Int. Cl.[4] .......................... C07C 12/02; C07C 4/12
[52] U.S. Cl. .................................. 585/322; 585/415; 585/483
[58] Field of Search .................... 585/322, 415, 483

[56] References Cited

U.S. PATENT DOCUMENTS

| | | | |
|---|---|---|---|
| 2,992,283 | 7/1961 | Eng | 260/673 |
| 3,160,671 | 12/1964 | Feigelman | 260/672 |
| 3,284,526 | 11/1966 | Frayer | 260/672 |
| 3,761,389 | 9/1973 | Rollmann | 208/64 |
| 4,157,356 | 6/1979 | Bulford et al. | 585/415 |
| 4,158,026 | 6/1979 | Addison | 585/321 |
| 4,180,689 | 12/1979 | Davies et al. | 585/407 |
| 4,329,532 | 5/1982 | Conn et al. | 585/407 |
| 4,347,394 | 8/1982 | Detz et al. | 585/419 |
| 4,451,685 | 5/1984 | Nevitt et al. | 585/415 |
| 4,528,412 | 7/1985 | Steacy | 585/415 |
| 4,579,988 | 4/1986 | Kieffer | 585/415 |

OTHER PUBLICATIONS

Csicery, Sigmund M., "Dehydrocyclodimerization", Ind. Eng. Chem. Process Des. Dev., vol. 18, No. 2, 1979, pp. 191-197.

Primary Examiner—Curtis R. Davis
Attorney, Agent, or Firm—Thomas K. McBride; John F. Spears, Jr.

[57] ABSTRACT

A process is disclosed for the conversion of a light aliphatic hydrocarbon, such as propane, into benzene and optionally also naphthalene. The feed hydrocarbon is converted to aromatic hydrocarbons in a dehydrocyclodimerization zone. The aromatics, and other cyclic hydrocarbons, are passed into a hydrodealkylation zone which is preferably supplied with hydrogen produced in the dehydrocyclodimerization zone. Benzene may be separated from the effluent of the dehydrocyclodimerization zone prior to passage of the aromatics into the hydrodealkylation zone.

13 Claims, 1 Drawing Sheet

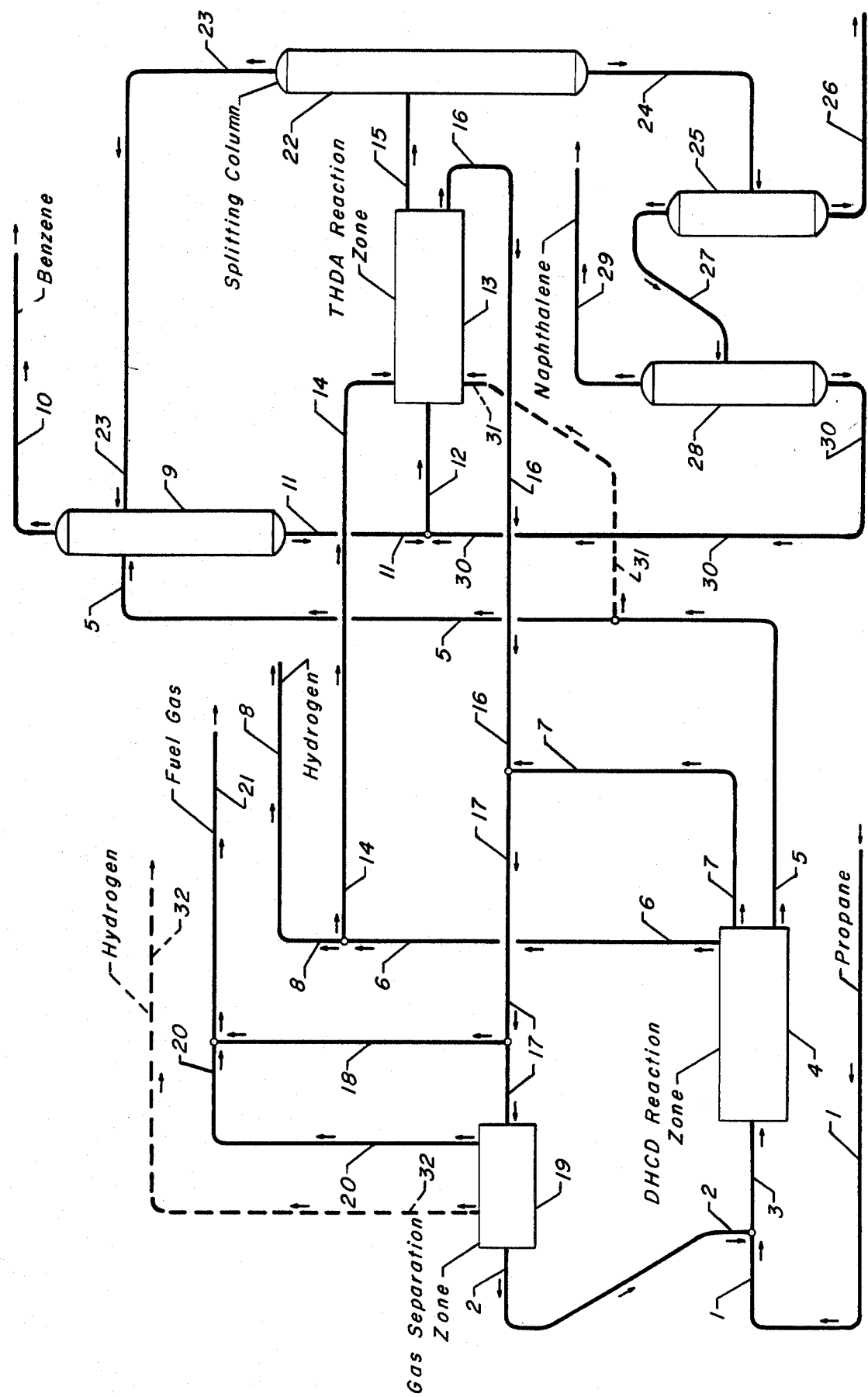

PRODUCTION OF BENZENE FROM LIGHT HYDROCARBONS

FIELD OF THE INVENTION

The subject process relates to a hydrocarbon conversion process. Specifically, the subject process relates to a process for the conversion of a light aliphatic hydrocarbon, such as propane or propylene, to benzene or to benzene and naphthalene. In a first conversion zone the light aliphatic hydrocarbons are converted to aromatic hydrocarbons by a dehydrocyclodimerization reaction, with hydrogen also being produced. In a second conversion zone, the resulting aromatic hydrocarbons other than benzene are subjected to a hydrodealkylation reaction which converts alkylaromatic hydrocarbons to benzene or naphthalene. The invention therefore relates to a process employing dehydrocyclodimerization and hydrodealkylation zones linked in a series flow arrangement.

INFORMATION DISCLOSURE

There are a large number of references which describe the conversion of light aliphatic hydrocarbons to aromatic hydrocarbons. For instance, U.S. Pat. No. 2,992,283 issued to J. Eng describes the conversion of propylene to a variety of higher molecular weight saturated and unsaturated hydrocarbons including aromatics using a treated crystalline aluminosilicate as the catalyst. U.S. Pat. No. 4,347,394 issued to C. M. Detz et al describes the conversion of $C_5$-plus hydrocarbons to aromatics using a nonacidic zeolite supporting a platinum compound. U.S. Pat. No. 4,451,685 issued to T. D. Nevitt et al presents a process for conversion of ethylene and/or propylene to gasoline blending stocks over a crystalline borosilicate catalyst containing specific metals. U.S. Pat. No. 4,329,532 issued to P. J. Conn et al describes the conversion of $C_4$-minus olefins or mixtures of olefins and paraffins to aromatic hydrocarbons using a catalyst which comprises a crystalline silicate having a specified composition, crystallite size range, and X-ray diffraction pattern.

A review of dehydrocyclodimerization was published at p. 191 of Volume 18, No. 2 (1979) of *Industrial and Engineering Chemistry—Process Design and Development* by S. M. Csicery. U.S. Pat. No. 4,180,689 issued to E. E. Davies et al describes the conversion of $C_3$-$C_8$ aliphatic hydrocarbons to aromatic hydrocarbons in a process which employs a catalyst comprising gallium supported on an aluminosilicate. U.S. Pat. No. 4,157,356 issued to S. N. Bulford provides similar teaching for a gallium on silica catalyst. U.S. Pat. No. 4,579,988 teaches the use of a crystalline gallium silicate catalyst for converting $C_2$-$C_4$ hydrocarbons to aromatics. U.S. Pat. No. 3,761,389 issued to L. D. Rollman et al describes an improved process for converting $C_2$ to 400° Fahrenheit hydrocarbons to aromatics over a ZSM-5 type catalyst.

U.S. Pat. No. 4,528,412 issued to P. C. Steacy is pertinent for its description of a product recovery method for dehydrocyclodimerization processes.

Hydrodealkylation processes are employed commercially for the production of benzene and naphthalene. These processes comprise the passage of an alkylaromatic charge stock and hydrogen through a reaction zone operated at conditions which promote the conversion of the alkyl side chains of the compound into light hydrocarbons such as methane and ethane. The side chains are thereby removed leaving cyclic product compounds. The process is described in some detail in U.S. Pat. No. 3,160,671 issued to S. I. Feigelman et al. and in U.S. Pat. No. 3,284,526 issued to J. A. Frayer et al.

U.S. Pat. No. 4,158,026 issued to G. E. Addison is pertinent for its showing of a combination process employing a hydrodealkylation reaction zone to increase the production of benzene. In this specific process, a naphtha boiling range feed stream is first passed through a catalytic reforming reactor to produce a mixture of aromatic hydrocarbons. The effluent of the reforming reactor enters a hot flash separation zone with a liquid phase stream removed from the hot flash separation zone being passed into a dealkylation reactor. The process thereby allows the production of a mixture of naphtha boiling range hydrocarbons having a higher concentration of benzene than would be provided by employing only the catalytic reforming reaction zone.

BRIEF SUMMARY OF THE INVENTION

The invention is a unique process for the production of benzene or benzene and naphthalene from a feed stream comprising light aliphatic hydrocarbons such as a mixture of propane and propylene or a mixture of propane and butane. One of the novel features of the subject invention is the integration of a catalytic dehydrocyclodimerization reaction zone with a thermal hydrodealkylation zone, with hydrogen and selected aromatic hydrocarbons produced in the dehydrocyclodimerization zone being charged to the hydrodealkylation zone for the production of benzene or for the production of benzene and naphthalene. One broad embodiment of the subject invention may be characterized as a process which comprises the steps of passing a feed stream comprising a $C_2$-$C_5$ aliphatic hydrocarbon into a dehydrocyclodimerization zone maintained at dehydrocyclodimerization conditions; concentrating at least 90 mole percent of the toluene produced in the dehydrocyclodimerization zone into a first process stream; passing the first process stream or a portion thereof and a hydrogen-rich gas stream into a hydrodealkylation zone operated at hydrodealkylation conditions and producing a second process stream, which stream comprises benzene and $C_7$-$C_{12}$ cyclic hydrocarbons; and, separating the second process stream in a separation zone and recovering benzene from the second process stream as a first product stream. A second embodiment of the subject invention may be characterized as a hydrocarbon conversion process which comprises the steps of passing a feed stream comprising a $C_2$-$C_5$ aliphatic hydrocarbon into a dehydrocyclodimerization zone maintained at dehydrocyclodimerization conditions and producing a first effluent stream comprising benzene, toluene, xylenes and $C_9$-$C_{12}$ cyclic hydrocarbons; separating the first effluent stream in a first separation zone, and producing a first product stream comprising benzene and a first process stream comprising toluene, xylenes and $C_{10}$-$C_{12}$ cyclic hydrocarbons; passing the first process stream or a portion thereof into a hydrodealkylation zone operated at hydrodealkylation conditions and producing a second effluent stream comprising benzene and $C_7$-$C_{12}$ cyclic hydrocarbons; separating the second effluent stream in a second separation zone and producing a second process stream comprising benzene, and passing at least a portion of the second process stream into the first separation zone and recovering benzene from the second effluent stream.

BRIEF DESCRIPTION OF THE DRAWING

The Drawing is a simplified process flow diagram illustrating several embodiments of the invention. In the basic flow of the process, propane entering through line 1 is converted to a mixture of aromatic hydrocarbons and hydrogen in the dehydrocyclodimerization zone 4 to produce benzene recovered by fractionation in the column 9 and alkylaromatics passed into a thermal hydrodealkylation reaction zone 13.

DETAILED DESCRIPTION

Dehydrocyclodimerization processes have been developed for the conversion of light aliphatic hydrocarbons to aromatic or nonaromatic $C_6$-plus hydrocarbons. The basic utility of these processes is the ability to convert low value highly available $C_3$ and/or $C_4$ hydrocarbons into more valuable aromatic hydrocarbons and hydrogen. The aromatic hydrocarbons are useful as gasoline-blending components and as feedstocks to petrochemical processes producing a variety of compounds consumed in plastics, paints, detergents, etc. The process may therefore be performed simply to upgrade the value of the hydrocarbons. It may also be desired to correct an overabundance of $C_3$ and $C_4$ hydrocarbons or to fulfill a need for the aromatic hydrocarbons. The aromatic hydrocarbons are highly useful in the production of a wide range of petrochemicals, with benzene being one of the most widely used. In some geographic locations, especially some Asian locations, there is only a minimal demand for $C_4$ olefins while there is a sizable market for both LPG and aromatic hydrocarbons. In this situation, it may be preferable to process available $C_4$ hydrocarbons to produce aromatics despite the inherent loss or degradation which results in the production of light hydrocarbons as by-products.

The dehydrocyclodimerization reaction produces a broad spectrum of aromatic hydrocarbons. If the product aromatic hydrocarbons are intended for use in a chemical complex, then many of the aromatic hydrocarbons produced by the dehydrocyclodimerization process would be compounds other than the desired feed compounds to the downstream petrochemical process. As previously mentioned, one of the most commonly used petrochemical feedstocks is benzene. It is accordingly an objective of the subject invention to provide a process for the conversion of light aliphatic hydrocarbons which produces a disproportionately high percentage of benzene. It is a further objective of the subject invention to provide a process for the conversion of light aliphatic hydrocarbons into benzene and naphthalene. The naphthalene would be produced by the conversion of alkylnaphthalenes produced in the dehydrocyclodimerization reaction. Naphthalene is considered a valuable feedstock in the production of phthalic anhydride, naphthol, insecticides, and specialty chemicals.

In the subject process the feed aliphatic hydrocarbons are first passed into a dehydrocyclodimerization zone which converts a significant portion of the entering hydrocarbons into aromatic hydrocarbons. The term "reaction zone" is intended to indicate the totality of the equipment employed in the conversion step wherein the feed hydrocarbons are passed through a reaction chamber, which may contain a catalyst, and the resultant hydrocarbons and any hydrogen are subsequently subjected to a series of steps including partial condensation and vapor-liquid separation for the generation of a liquid phase reaction zone effluent stream and preferably one or more vapor-phase streams. As used herein, the term "reaction zone" is also intended to include a product stripping column located immediately downstream of vapor-liquid separation devices employed within the reaction zone when the use of such a stripping column within the reaction zone is desired.

The function of these separatory systems within the reaction zone is primarily to recover hydrogen for removal from the reaction zone or internal circulation within the reaction zone and also for the removal of light by-products such as methane and ethane from the liquid phase products of the reaction zones. Both the dehydrocyclodimerization or DHCD reaction zone and the thermal hydrodealkylization or THDA reaction zone may employ a stripping column to separate the light gases commonly referred to as fuel gas from the liquid phase products. Alternatively, only a bulk partial condensation and phase separation may be preferred depending on such factors as utility (electricity, steam) costs, product distribution, feedstock costs, product values, etc. An engineering analysis based upon these and other factors which vary between installations must be performed to determine an optimum separation and product recovery flowscheme. This potential variety results in the alternative embodiments of the drawing. When a bulk separation is used, the vapor-phase portion of the reaction zone effluent of the dehydrocyclodimerization zone is preferably separated by passage into a "cold box" to yield a hydrogen stream, light off gases and feed hydrocarbons for recycling to the reaction zone.

The composition of the effluent stream of the dehydrocyclodimerization zone will depend upon such factors as reactor operating conditions and the composition of the feedstock. For instance, at relatively low reactor operating temperatures, the presence of olefinic hydrocarbons within the feedstream would tend to cause the production of branch chain (acyclic) $C_6+$ hydrocarbons in addition to the desired aromatic hydrocarbons. When processing a feedstream comprising propane or butane or mixtures thereof, the reaction zone effluent stream will contain benzene, toluene, ethylbenzene, a mixture of the various xylenes, styrene, N-propyl benzene, cumene, methylethyl benzene, trimethyl benzenes, methyl propyl benzenes, dimethylethyl benzenes, indane, $C_{11}$ alkylbenzenes, naphthalene, methylnaphthalene, dimethylnaphthalene and a very small amount of heavier aromatic compounds. When processing a feedstream of pure propane and/or butane at preferred reactor temperatures, the $C_6+$ liquid product composition should contain less than 0.5 weight percent of nonaromatics.

The $C_6+$ liquid phase hydrocarbons which form the effluent stream of the DHCD reaction zone are preferably passed into a first fractionation column which is operated at conditions effective to separate the entering the $C_6+$ hydrocarbons into a high-purity net overhead stream of benzene and a net bottoms stream comprising the remainder of the hydrocarbons which enter the fractionation column. This benzene recovery column produces the major product stream of the process. It also concentrates the heavier $C_7+$ hydrocarbons into the net bottoms stream which is combined with other heavy recycle hydrocarbons and passed into the THDA (thermal hydrodealkylation) reaction zone. As shown in the drawing, it may in some instances be preferred to pass the liquid phase $C_6+$ portion of the DHCD effluent directly into the THDA zone. This may occur when the as-produced benzene would not satisfy a product specification. In other instances, it may be desired to employ two or more fractionation columns during the separation of the $C_6+$ effluent of the DHCD zone. For example, the bottoms stream of the benzene recovery column can be fractionated in a second column with the toluene-rich overhead product of the second column being charged to the THDA and the $C_8+$ net bottoms stream being removed as a xylene-containing product stream.

The THDA reaction zone is operated at conditions which effect the removal of alkyl groups from the various cyclic compounds charged thereto. Hydrogen is passed through the THDA zone to prevent the condensation of alkylaromatics into heavier compounds and to generally prevent coke formation. Hydrogen is also passed through the reaction zone to satisfy the hydrogen consumption demands which result from the breakage of various bonds along the alkyl side chains and at the point that the alkyl side chain is attached to the cyclic hydrocarbons. The branched chain compounds are broken down into smaller fragments such as methane, ethane, and propane. This material is concentrated into a fuel gas stream through the use of vapor-liquid separation zones and a product stripping column. The major effluent stream of the THDA reaction zone is therefore, after partial condensation and separation, a $C_6+$ liquid phase stream comprising a mixture of the various hydrocarbons but having a much higher concentration of benzene and naphthalene than the feedstream to the THDA reaction zone. This effluent stream is preferably passed into a second fractionation zone which concentrates the benzene into a stream passed into the benzene recovery column of the first fractionation zone. The arrangement of the second fractionation zone is dependent upon several factors such as whether it is desired to recover a naphthalene product stream and/or to reject various $C_{12}+$ hydrocarbons from the process as a drag stream. As used herein the term "rich" is intended to indicate a concentration of the specified compound or class of compounds greater than 60 mole percent and preferably greater than 80 mole percent.

The drawing illustrates several different embodiments of the invention including several optional process lines used in variations of the process and which can be totally deleted if so desired. Referring now to the drawing, a feedstream of propane representing the numerous feedstream compositions which may be passed into the process is directed into a DHCD reaction zone 4 through lines 1 and 3. Within the DHCD reaction zone, the feedstream is contacted with a catalyst under dehydrocyclodimerization conditions effective to convert a significant portion of the propane to aromatic hydrocarbons. This reaction step also releases hydrogen. Within the reaction zone, the effluent of the reactor is partially condensed and separated into vapor and liquid phase portions. A gas stream rich in hydrogen is removed from the reaction zone 4 through line 6. Light hydrocarbons produced as a by-product of the dehydrocyclodimerization reactions and unconverted propane are concentrated into a second gas stream removed from the reaction zone through line 7. The product $C_6+$ aromatic hydrocarbons are removed from the bottom of a stripping column present within the reaction zone and are passed through line 5 into the benzene recovery column 9.

The hydrocarbons entering the benzene recovery column 9 are separated into a high-purity benzene net overhead stream removed through line 10 and a net bottoms stream removed through line 11. The net bottoms stream of line 11 should contain all of the $C_7+$ hydrocarbons which enter column 9. The hydrocarbons flowing through line 11 are admixed with a process stream flowing through line 30 which comprises an admixture of $C_{11}$ and $C_{12}$ aromatic hydrocarbons. The admixture of these two streams is then passed through line 12 into the thermal hydrodealkylation (THDA) reaction zone 13. Also passed into the THDA zone is a stream of high-purity hydrogen from line 14. This hydrogen is derived from the DHCD reaction zone off-gas stream of line 6, with the portion not required in the THDA zone being removed through line 8 as a hydrogen product stream. Optional line 31 is shown to illustrate the process flow employed if it is desired to pass the $C_6$-plus portion of the DHCD reaction zone effluent directly into the THDA reaction zone.

Within the THDA reaction zone the hydrocarbons of line 12 and the hydrogen of line 14 are passed through a thermal reaction zone wherein alkyl groups are split off of the aromatic ring structures and cracked to relatively light hydrocarbons. The effluent of the thermal reactor is partially condensed and separated in a vapor-separation zone not shown to yield an off-gas stream removed from the process through line 16. The liquid material collected in the vapor-liquid separator is passed into a stripping column not shown which is also located within the THDA reaction zone as previously described. In the stripping column $C_5$-hydrocarbons are removed as a net overhead gas stream which is combined with the off-gas stream of line 16 and removed from the THDA reaction zone. This produces a net bottoms stream compiising an admixture of $C_6+$ aromatic hydrocarbons which is removed from the THDA reaction zone through line 15 as the effluent stream of this reaction zone. This effluent stream is passed into the splitting column 22. The splitting column 22 is designed and operated to effect the separation of the entering hydrocarbons into a net overhead stream removed through line 23 which comprises essentially all of the benzene and $C_7$ to $C_{11}$ alkylbenzene hydrocarbons entering the column and a net bottoms stream removed through line 24 which comprises essentially all of the $C_{10}+$ alkyl naphthalenes entering the column. This results in recycling the $C_7$–$C_{10}$ alkylbenzenes via lines 11 and 12.

The overhead stream of line 23 is passed into the benzene recovery column 9 to allow the recovery of the benzene produced in the THDA reaction zone in the overhead product stream of line 10. $C_9$ to $C_{10}$ hydrocarbons carried by line 23 are recycled to the THDA reaction zone through lines 11 and 12. The fractionation methods employed to separate the material removed as the net bottoms stream of the splitting column is subject to significant variation. The fractionation method illustrated in the drawing is preferred. In this method, the $C_{10}+$ hydrocarbons of line 24 are passed into a first fractional distillation column 25 which produces a relatively small net bottoms stream comprised of $C_{12}+$ hydrocarbons typified by biphenyl and dimethyl naphthalene. This net bottoms stream is withdrawn from the process through line 26 as a drag stream as the continued recycling of these materials into the THDA reaction zone would have adverse effects upon the process. Optionally, a portion of the material concentrated into the stream of line 26 may be recycled by passage through a line not shown in admixture with the material flowing through line 30.

The net overhead product stream of column 25 comprises such compounds as naphthalene and methylnaphthalene. This overhead stream is passed through line 27 into a second fractional distillation column 28 wherein it is separated into a relatively high-purity net overhead product stream comprising naphthalene which is withdrawn from the process through line 29. The methylnaphthalenes concentrated into the net bottoms stream of the fractionation column 28 are removed through line 30 for recycling to the THDA reaction zone. The recycling results in essentially all $C_7$ to $C_9$ hydrocarbons present in the THDA reaction zone effluent stream being recycled to the THDA zone.

The light hydrocarbons produced in the DHCD zone and the THDA zone would normally be vended from the respective zones as off-gas streams removed from the process. However, they could be collected by combining the gas flows of lines 16 and 7 to form a composite stream passed through line 17 into a gas separation zone 19. Within the gas separation zone, the entering light hydrocarbons can be separated as through pressure swing adsorption, the use of membrane separation techniques or by cryogenic (cold box) techniques to produce a gas stream predominating in $C_3+$ hydrocarbons which is passed through line 2 to the inlet to the DHCD reaction zone. The remaining lighter gases such as methane and ethane are vented from the gas separation zone through line 20 and combined with any portion of the net off-gases which are bypassed around the gas separation zone through line 18. This produces the net fuel gas stream of line 21. A hydrogen-rich gas stream will normally be produced in such a gas separation zone and removed through optional (therefore dashed) line 32. In many instances the use of a gas separation zone would be preferred and the gas stream of line 6 would not be provided. Hydrogen for use in the THDA zone would be derived from line 32.

The feed compounds to the dehydrocyclodimerization zone are light aliphatic hydrocarbons having from 2 to 5 carbon atoms per molecule. Feed streams may comprise a single compound or a mixture of two or more of these compounds. The preferred feed compounds for the subject process are propane and/or the butanes. Butylenes and/or propylenes may be present in the feed stream. The feed stream to the process may also contain some $C_2$ and $C_5$ hydrocarbons. It is preferred that the concentration of $C_5$ hydrocarbons in the feed stream to the subject dehydrocyclodimerization process is held to the minimum practical level. It is also pertinent in this regard to note that U.S. Pat. No. 4,565,897 is specifically directed to a dehydrocyclodimerization process wherein the feedstream contains from between 10 to 50 weight percent ethane.

The configuration of the dehydrocyclodimerization reaction zone and the composition of the catalyst employed within the reaction zone are not basic elements of the invention or limiting characteristics of the invention. Nevertheless, in order to provide a background to the subject invention, it is felt useful to describe the preferred reactor system for use in the invention. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,909. These patents also describe catalyst regeneration systems and various aspects of moving catalyst bed operations and equipment. This reactor system is widely employed commercially for the reforming of naphtha fractions. Its use has also been described for the dehydrogenation of light paraffins.

The preferred moving bed reactor system employs a spherical catalyst having a diameter between about 1/64 and 1/8 inch. The catalyst preferably comprises a support material and a metallic component deposited on the support material as through impregnation or coprecipitation. The previously cited references point out that the current trend is the use of a zeolitic support material, with the catalyst referred to in the art as a ZSM-5 type zeolite being often specified as a preferred material. When properly formulated, it appears this zeolitic material by itself has significant activity for the dehydrocyclodimerization reaction. Further information on such zeolitic catalysts for the DHCD reaction can be obtained from European Patent Application No. 83 20114229 by E. P. Kieffer. However, it is still preferred to employ a metallic component within the catalyst system to increase the aromatic selectivity of the catalyst. The preferred metallic component is gallium as described in the previously cited U.S. Pat. No. 4,180,689. The catalyst may contain from about 0.15 to 2.4 weight percent gallium which is preferably exchanged or impregnated into the zeolitic component of the catalyst rather than forming a portion of the original (as produced) zeolite. A preferred range of the gallium component is from 0.3 to 1.0 weight percent. Further information on catalysts and operating conditions for the DHCD zone may be obtained from U.S. Pat. No. 4,565,897 which is incorporated herein by reference.

The zeolitic material, preferably ZSM-5, is normally bound during the particle forming stage with another material primarily to increase the strength and durability of the catalyst. This binding material is often a form of clay or alumina. It is highly preferred that this binder comprises a phosphorous-containing alumina, as can be prepared by the gelation of a hydrosol precursor in accordance with the well-known oil-dropping method. For instance, $H_3PO_4$ may be admixed with an alumina hydrosol prepared by digesting aluminum in aqueous hydrochloric acid and/or aluminum chloride solution. The finished catalyst should have a phosphorous to aluminum ratio of from about 1:1 to about 1:100. The aluminosilicate or zeolite can be present in the hydrosol prior to admixture with the phosphorous-containing compound or the zeolite can be admixed into the phosphorous-containing alumina. The final composite can be formed in a variety of shapes or by oil-dropping and finished using conventional catalyst manufacturing techniques.

The dehydrocyclodimerization reaction zone is preferably operated at a temperature between about 850 degrees–1100 degrees Fahrenheit (454 degrees–593 degrees Celsius) and a pressure under 120 psig (827 kPa g). Hydrogen-producing reactions are normally favored by lower pressures, and pressures under about 70 psig (483 kPa g) at the outlet of the reaction zone are highly preferred. Optimum conditions will depend upon the feed and catalyst.

It is believed that those skilled in the art of petroleum and petrochemical process design may determine proper operating conditions, vessel designs, and operating procedures for the product recovery and separation steps of the subject process through the use of standard process design techniques after having now been appraised of the overall flow of the process. The materials being processed are very common and frequently subjected to similar process steps. The fractionation zones employed in the process preferably contain a single trayed fractionation column having sieve-type trays and being of relatively standard design. For instance, a properly designed column having 30 trays will function as the splitting column, and the benzene product recovery column may contain about 40 trays. Suitable fractionation zones may be readily designed by those skilled in the art. The operating conditions required in the fractionation zones are dependent upon the compounds being separated and the desired separation.

The dealkylation reaction is exothermic in nature. The dealkylation reaction is also hydrogen-consuming with the hydrogen being consumed in the saturation of the unsaturated fragments produced by the cracking of portions of the alkyl side chain or the removal of the alkyl side chain from the cyclic hydrocarbons. To prevent the formation of olefinic hydrocarbons, hydrogen is added to the dealkylation reaction zone and the overall reaction is therefore referred to as hydrodealkylation. Hydrodealkylation operating temperatures would normally range from about 1,000 degrees Fahrenheit (538 degrees Celsius) to about 1,500 degrees Fahrenheit (815 degrees Celsius) at the inlet to the reaction vessel. The dealkylation conditions also include a pressure of from about 300 psig (2069 kPa) to about 1,000 psig (6895 kPa g) and a liquid hourly space velocity preferably in the range of about 0.5 to about 5.0 based upon available internal volume of the reaction vessel(s).

Both thermal and catalytic hydrodealkylation processes are known in the art. The dealkylation zone may therefore contain a bed of a solid catalyst such as the catalyst described in U.S. Pat. No. 3,751,503. However, it is greatly preferred that the dealkylation reaction chambers are devoid of solid catalytic material. Due to the exothermic nature of the dealkylation reaction, it is often required to perform the overall dealkylation in two or more stages with intermediate cooling or clenching of the reactants. The two or three or more reaction vessels can therefore be used in series. The cooling may be achieved by indirect heat exchange or interstage cooling. The preferred mode of cooling the reactants is by the injection of a small portion of the feed aromatic hydrocarbons at a rate and temperature calculated to reduce the temperature of the resultant reaction admixture to the desired inlet temperature for the second reaction vessel. When two reaction vessels are employed in the dealkylation zone it is preferred that the first vessel is essentially devoid of any internal structure and that the second vessel contains sufficient internal structure to promote plug flow of the reactants through a portion of the vessel.

A more limited embodiment of the invention may accordingly be characterized as a process for the production of benzene which comprises the steps of passing a feed stream comprising a $C_2$-$C_4$ aliphatic hydrocarbon into a dehydrocyclodimerization zone comprising a bed of solid catalyst and producing a first conversion zone product stream comprising benzene, toluene and $C_9$-$C_{12}$ cyclic hydrocarbons including naphthalene, and also producing a hydrogen-rich gas stream; passing the first conversion zone product stream into a first fractional distillation zone operated at conditions effective to separate entering hydrocarbons into a first fractionation zone product stream, which is rich in benzene, and a first process stream, which comprises toluene and $C_9$-$C_{12}$ cyclic hydrocarbons; passing the first process stream and at least a portion of the hydrogen-rich gas stream into a thermal hydrodealkylation zone operated at hydrodealkylation conditions, and producing a second conversion zone product stream comprising benzene and $C_9$-$C_{12}$ cyclic hydrocarbons including naphthalene; passing the second conversion zone product stream into a second fractional distillation zone operated at conditions effective to separate entering hydrocarbons into a second process stream comprising benzene, a third process stream comprising $C_{11}$ alkyl naphthalenes and a second fractionation zone product stream comprising naphthalene, which is withdrawn from the process; passing the second process stream into the first fractional distillation zone; and passing the third process stream into the hydrothermaldealkylation zone. The second process preferably also comprises $C_7$-$C_{10}$ alkylbenzenes. Essentially all of the $C_7$-$C_9$ hydrocarbons and more specifically essentially all of the $C_7$-$C_{10}$ alkylbenzenes are preferably recycled to the hydrodealkylation zone from the second distillation zone.

The illustration of the flow of the subject process presented in the drawing has been simplifed by the deletion of many required pieces of equipment which are not believed pertinent or necessary to a discussion of the subject invention. These engineering features include control systems, pumps and compressors, reactor and fractionation column internals, overhead condensing systems and reboiling systems for the fractionation columns and similar process equipment of a generalized nature. Also not illustrated on the drawing is a clay treating zone. As is known in the art, it will normally be desirable to clay treat the effluent from a dealkylation zone to meet color specifications for the products. The clay treating equipment may be located between the stripping column and the fractionation column of the dealkylation or may be located so to treat just the effluent streams discharged from the process.

The relative distribution of the products produced in the subject process will be dependent upon several factors including the compostion of the feedstream, the effectiveness of the DHCD catalyst and the operating conditions employed within the DHCD reaction zone and the fractionation schemes employed within the process flow. If the process is operated to coproduce both benzene and naphthalene from a feedstream of propane, the following product distribution is to be expected. Based upon the production of 100,000 mta (metric tons per atom) of benzene, there will be coproduced 8,353 mta naphthalene, 9,064 mta of 97% purity hydrogen gas, 85,155 mta of light ends and 793 mta of bicyclic compounds removed as dragstreams from the process.

It is apparent from this projected production slate that the subject process will produce a significant quantity of light ends such as methane, ethane, propane and butane. The predominant compounds in the light ends will be methane and ethane. Accordingly, in one embodiment of the invention all or a portion of the light ends produced in the THDA reaction zone together with all or a portion of the light ends in the DHCD reaction zone may be recycled to the DHCD reaction zone for the production of additional quantities of aromatic hydrocarbons. The previously described product distribution is based upon no recycling of these light hydrocarbons and would change depending upon the amount of recycling and the amount of conversion of these light hydrocarbons achieved in the DHCD reaction zone. It is presently not preferred to pass methane into the DHCD reaction zone. Therefore, it is preferred to separate methane to the extent economically feasible from any recycled gases.

As previously mentioned, this separation can be performed in a number of different ways including pressure swing adsorption, partial condensation through the use of low temperatures in a cryogenic separation system similar to the "cold boxes" employed for gas recovery and separation, or through the use of membranes which selectively allow the passage of one or more types of hydrocarbons. The use of a low temperature separation technique is preferred. In this technique, the gases to be recycled would preferably be compressed, cooled and then flashed to generate low temperature fluids which would be used to achieve the condensation of ethane. Reference may be made to U.S. Pat. No. No. 4,528,412, which is incorporated herein by reference, and illustrates a low temperature gas separation technique suitable for separating light gases. In this reference, a bottom stream from a stripping column contains propane and butane recovered by this technique in addition to a variable amount of ethane, with this bottom stream being suitable for recycling to the DHCD reaction zone of the process described therein. The use of pressure swing adsorption in the separation of the gases produced in a DHCD reaction zone is described in U.S. Pat. No. 4,547,205.

I claim as my invention:

1. A hydrocarbon conversion process which comprises the steps of:
    (a) passing a feed stream comprising a $C_2$-$C_5$ aliphatic hydrocarbon into a dehydrocyclodimerization zone maintained at dehydrocyclodimerization conditions;
    (b) concentrating, in a first separation zone comprising a first fractionation column, at least 90 mole percent of the toluene produced in the dehydrocyclodimerization zone into a first process stream and benzene into a benzene-rich first product stream;
    (c) passing the first process stream and a hydrogen-rich gas stream directly into a hydrodealkylation zone operated at hydrodealkylation conditions and producing a second process stream, which stream comprises benzene and toluene; and,
    (d) passing the second process stream directly into a second separation zone comprising a second fractionation column, passing a third process stream, comprising benzene, from the second fractionation column to the first fractionation column, and recovering benzene from the second process stream as a portion of a first product stream.

2. The process of claim 1 wherein the second process stream comprises $C_8$-$C_{12}$ cyclic hydrocarbons including $C_8$-$C_{10}$ alkylbenzene hydrocarbons and is separated by fractional distillation within the second separation zone and a third process stream which is rich in aromatic hydrocarbons having over 11 carbon atoms is produced in the second separation zone and withdrawn from the process.

3. The process of claim 2 wherein a second product stream comprising naphthalene is also produced in the second separation zone and withdrawn from the process.

4. The process of claim 3 further characterized in that essentially all $C_7$ to $C_{10}$ alkylbenzene hydrocarbons present in the seocnd process stream are recycled to the hydrodealkylation zone.

5. The process of claim 1 wherein the hydrodealkylation zone is operated without the use of any catalyst.

6. The process of claim 5 wherein a bed of a catalyst comprising gallium is present within a reaction zone of the dehydrocyclodimerization zone.

7. A process for the production of benzene which comprises the steps of:
    (a) passing a feed stream comprising a $C_2$-$C_4$ aliphatic hydrocarbon into a dehydrocyclodimerization zone comprising a bed of solid catalyst and producing a first conversion zone product stream comprising benzene, toluene and $C_9$-$C_{12}$ cyclic hydrocarbons including naphthalene, and also producing a hydrogen-rich gas stream;
    (b) passing the entire first conversion zone product stream into a first fractional distillation zone operated at conditions effective to separate entering hydrocarbons into a first fractionation zone product stream, which is rich in benzene, and a first process stream, which comprises toluene and $C_9$-$C_{12}$ cyclic hydrocarbons;
    (c) passing the first process stream and at least a portion of the hydrogen-rich gas stream into a hydrodealkylation zone operated at hydrodealkylation conditions, and producing a second conversion zone product stream comprising benzene and $C_9$-$C_{12}$ cyclic hydrocarbons including naphthalene;
    (d) passing the second conversion zone product stream directly into a second fractional distillation zone operated at conditions effective to separate entering hydrocarbons into a second process stream comprising benzene, a third process stream comprising $C_{11}$ alkylnaphthalenes and a second fractionation zone product stream comprising naphthalene, which is withdrawn from the process;
    (e) passing the second process stream into the first fractional distillation zone; and,
    (f) passing the third process stream into the hydrodealkylation zone.

8. The process of claim 7 wherein the hydrodealkylation zone is devoid of catalyst.

9. The process of claim 8 wherein a third fractionation zone product stream comprising $C_{12}$-plus alkylnaphthalenes compounds is produced in the second fractionation zone and removed from the process.

10. The process of claim 9 wherein the third fractionation zone product stream comprises biphenyl.

11. The process of claim 7 wherein a bed of a catalyst comprising gallium is employed within the dehydrocyclodimerization zone.

12. The process of claim 11 wherein the feed stream comprises propane.

13. The process of claim 7 wherein the second process stream comprises $C_7$-$C_{10}$ alkylbenzenes.

* * * * *